United States Patent
Chen et al.

(10) Patent No.: US 10,548,566 B2
(45) Date of Patent: Feb. 4, 2020

(54) SYSTEM AND METHOD FOR TRACKING SIGNAL OF WIRE IN A BLOOD VESSEL

(71) Applicant: METAL INDUSTRIES RESEARCH & DEVELOPMENT CENTRE, Kaohsiung (TW)

(72) Inventors: Ming-Hui Chen, Kaohsiung (TW); Ming-Hui Cheng, Kaohsiung (TW); Tzyy-Ker Sue, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 476 days.

(21) Appl. No.: 15/372,414

(22) Filed: Dec. 8, 2016

(65) Prior Publication Data

US 2018/0160937 A1    Jun. 14, 2018

(51) Int. Cl.
*A61B 5/00*          (2006.01)
*A61B 8/00*          (2006.01)

(52) U.S. Cl.
CPC .......... *A61B 8/4483* (2013.01); *A61B 5/0095* (2013.01)

(58) Field of Classification Search
CPC ....... A61B 8/4483; A61B 8/0891; A61B 8/12; A61B 8/4209; A61B 5/061; A61B 5/0095
See application file for complete search history.

(56) References Cited

U.S. PATENT DOCUMENTS

| | | | |
|---|---|---|---|
| 6,358,211 B1 | 3/2002 | Mamayek | |
| 8,016,814 B2 | 9/2011 | Blakstvedt et al. | |
| 8,172,757 B2 | 5/2012 | Jaffe et al. | |
| 2003/0007140 A1* | 1/2003 | Korenaga | G03F 7/70716 355/72 |
| 2004/0131299 A1* | 7/2004 | Adoram | A61B 8/0833 385/12 |
| 2007/0016068 A1 | 1/2007 | Grunwald et al. | |
| 2012/0265060 A1* | 10/2012 | Ramraj | A61B 6/0457 600/427 |
| 2018/0000444 A1* | 1/2018 | Dayton | A61B 8/0883 |

FOREIGN PATENT DOCUMENTS

| | | |
|---|---|---|
| TW | 270572 | 2/1996 |
| TW | 201223583 A | 6/2012 |
| TW | I529391 B | 4/2016 |
| TW | M531406 U | 11/2016 |

* cited by examiner

*Primary Examiner* — Pascal M Bui Pho
*Assistant Examiner* — John Denny Li
(74) *Attorney, Agent, or Firm* — CKC & Partners Co., LLC (57) ABSTRACT

The system includes a stand surrounding a working area, a signal detector receiving a signal generated by the wire, and a positioning module disposed on the stand. The positioning module is configured to drive the signal detector moving forward and backward on a two-dimensional plane in the working area. The system also includes a computer system electrically connected to the signal detector and the positioning module. The compute system receives the signal from the signal detector, generates position information according to the signal, and transmits the position information to the positioning module, such that the positioning module moves the signal detector to a position corresponding to a position of the wire in the blood vessel according to the position information.

4 Claims, 6 Drawing Sheets

SYSTEM AND METHOD FOR TRACKING SIGNAL OF WIRE IN A BLOOD VESSEL

BACKGROUND

Field of Invention

The present invention relates to a tracking system. More particularly, the present invention relates to a method and a system for tracking a wire in a blood vessel of a human body.

Description of Related Art

The World Health Organization (WHO) predicts that more than twenty-three million people will die due to cardiovascular diseases annually in the world before year 2030. Ministry of health and welfare in Taiwan predicts that number of the patient suffered from cardiovascular diseases will increase 0.5 million per year. The number of patients having cardiovascular disease has been the highest in the world in an aspect of demand side of medical market. The product demand for all kinds of wire/catheter has been increased for years, and the scale of the global market is nearly 28.6 billion dollars in 2014, and is predicted to be 42.4 billion dollars in 2019. Factors driving this wire/catheter market includes increasing need for minimally invasive procedures, increasing elderly population, and diseases such as obesity caused by lifestyle which results in the grow of cardiovascular diseases.

Minimally invasive surgery with cardiac catheterization is a main treatment for cardiovascular diseases. Take invasive treatment of coronary heart disease as an example, an arterial sheath (the diameter thereof is about 2 mm to 3 mm) is plugged into an artery in arm or groin, and a steel wire enters a treatment part through the blood vessel to establish a surgery channel. An instrument combined with a plastic catheter enters the blood vessel through the wire for diagnosis and treatment. Therefore, putting the wire into the treatment location through the blood vessel is the first step, and problems in the surgery includes: unidirectional operation which needs many trying; lots of product specification based on the context; large amount of X ray and developer are required; depend on doctor's experience and high risk. The massive using of X ray and developer may cause other organs (e.g. kidney) damaged. Therefore, it is an issue in the art about how to devise a method for tracking a wire in the human body to provide route guide during the surgery and decrease the amount the X ray and developer.

SUMMARY

Embodiments of the present invention provide a system for tracking a wire in a blood vessel in a human body. The system includes a stand surrounding a working area, a signal detector receiving a signal generated by the wire, and a positioning module disposed on the stand. The positioning module is configured to drive the signal detector moving forward and backward on a two-dimensional plane in the working area. The system also includes a computer system electrically connected to the signal detector and the positioning module. The compute system receives the signal from the signal detector, generates position information according to the signal, and transmits the position information to the positioning module, such that the positioning module moves the signal detector to a position corresponding to a position of the wire in the blood vessel according to the position information.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. In the specification should be understood for identifying units or data described by the same terminology, but are not referred to particular order or sequence. In addition, the term "couple" used in the specification should be understood for electrically connecting two units directly or indirectly. In other words, when "a first object is coupled to a second object" is written in the specification, it means another object may be disposed between the first object and the second object.

The invention provides a system including a stand, a signal detector, a positioning module and a computer system. A wire is put into a blood vessel of a human body, and the positioning module moves the signal detector to a position corresponding to the wire. As a result, healthcare providers just need to control the position of the wire with no need to move the signal detector.

Figure 1:
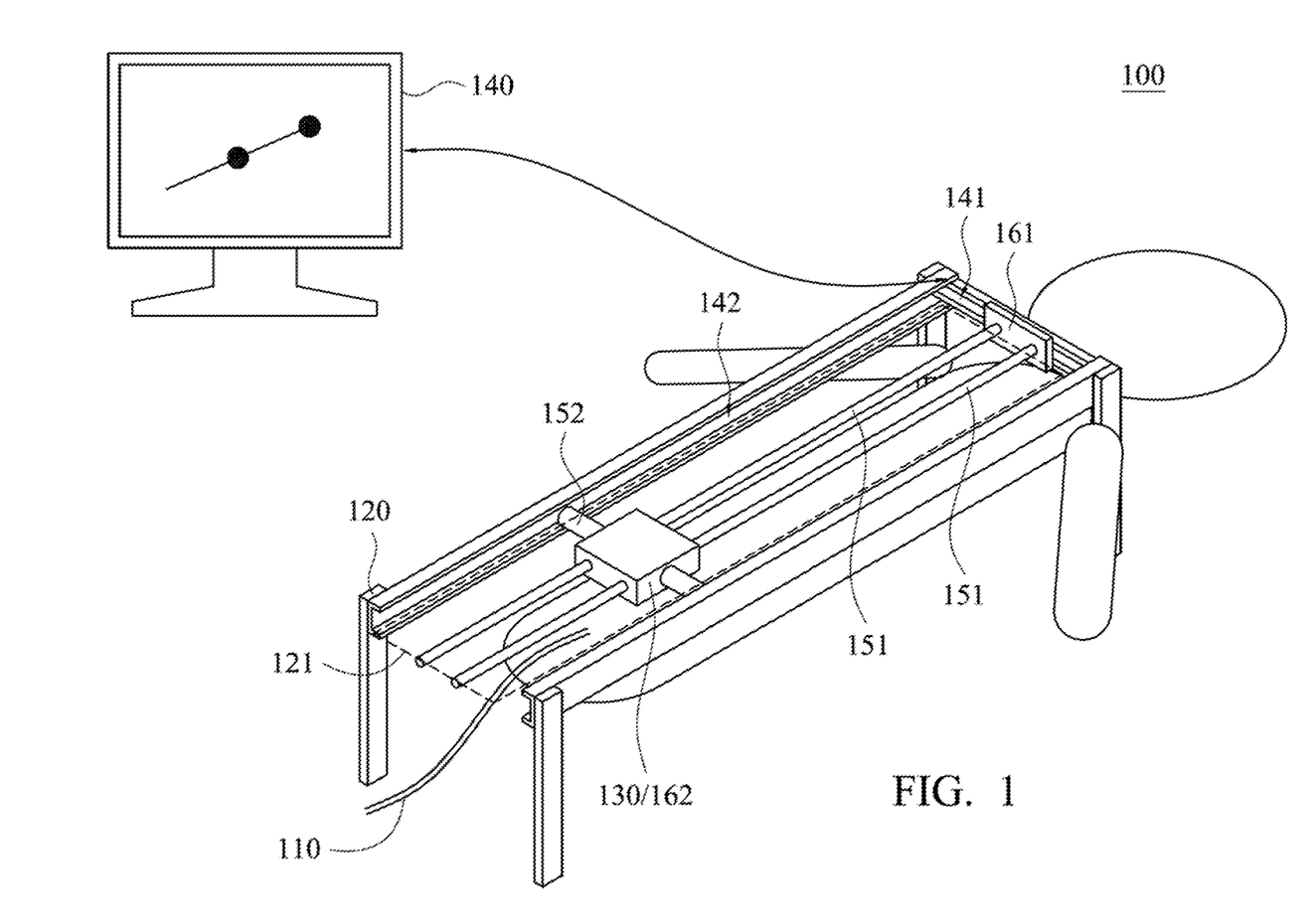
FIG. 1 is a schematic diagram illustrating a system for tracking a wire according to an embodiment.
Figure 2A:
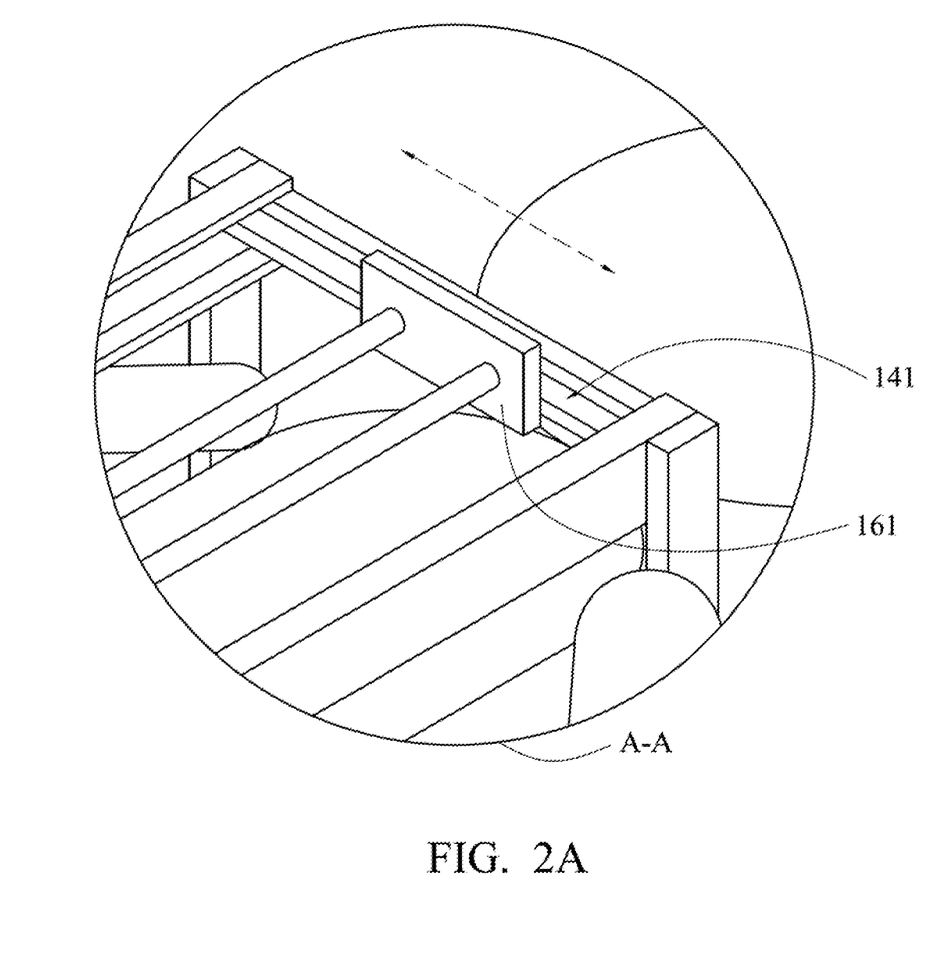
FIG. 2A and FIG. 2B are diagrams illustrating the positioning module moving the signal detector according to an embodiment.
Figure 2B:
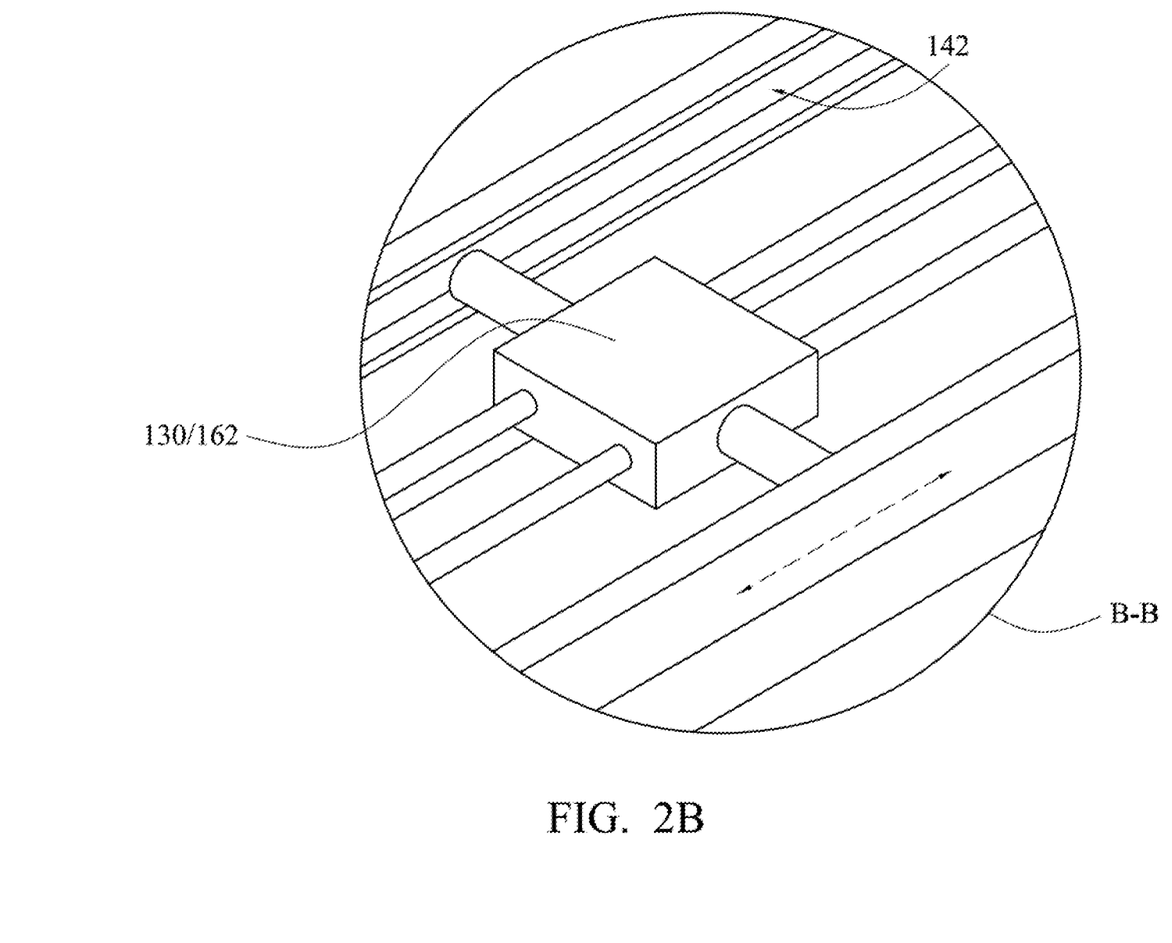

FIG. 1 is a schematic diagram illustrating a system for tracking a wire according to an embodiment. Referring to FIG. 1, a system 100 includes a wire 110, a stand 120, a signal detector 130 and a computer system 140. The stand 120 surrounds a working area 121, and a signal detector 130 moves forward and backward on any two-dimensional plane in the working area 121 to track the wire 110. To be specific, a first track 141 and a second track 142 are formed on the stand 120, the first track 141 and the second track 142 are essentially perpendicular to the each other, and the first track 141 and the second track 142 surround the working area 121. The aforementioned positioning module includes a first driving unit 161, a first support structure 151, a second driving unit 162 and a second support structure 152. The second driving unit 162 is connected to the signal detector 130. For simplification, the second driving unit 162 and the signal detector 130 are shown as a single unit. The first driving unit 161 and the second driving unit 162 are, for example, motors. The first support structure 151 and the second support structure 152 are, for example, rods with any materials, which is not limited in the invention. The first driving unit 161 is disposed in the first track 141, and the first support structure 151 is disposed perpendicular to the first track 141 and connected to the first driving unit 161. The first driving unit 161 moves along the first track 141 so that the first support structure 151 also moves along the first track 141. In addition, the second driving unit 162 is disposed on the first support structure 151. The second support structure 152 is disposed in the second track 142 and connected to the second driving unit 162. The second driving unit 162 moves along the first support structure 151 so that the second support structure 152 moves along the second track 142. The moving of the signal detector 130 is shown in FIG. 2A and FIG. 2B, in which areas A-A and B-B are enlarged diagrams with respect to the first driving unit 161 and the second driving unit 162 in FIG. 1 respectively. Consequently, the signal detector 130 is able to move to any position on a two-dimensional plane in the working area 121.

The first track 141 and the second track 142 are straight in the embodiment discussed above, but the tracks on the stand may have any other trajectories in other embodiments, and more or less driving unit may be disposed on the stand. For example, the first driving unit 161 may be omitted, and the second driving unit 162 also moves along with the second support structure 152 in order to move the first support structure 151 along the first track 141 in addition to move along the first support structure 151. The stand 120 and the positioning module of FIG. 1 are just examples, and the invention is not limited thereto.

In the embodiment, the signal detector 130 is an ultrasound detector, and the wire 110 is put into the blood vessel of the human body to generate an ultrasound signal. People in the art should be able to understand the ultrasound signal is a mechanical wave which is transformed into an electrical signal via the ultrasound detector. For simplification, the ultrasound signal mentioned in the specification may be mechanical wave or electrical signal, and the description will not be repeated. There are two ways to generate the ultrasound signal. The first one is based on photoacoustic effect, in which a tissues irradiated by light would generate the ultrasound signal due to expansion caused by the light. Therefore, the wire 110 may be an optical fiber configured to deliver light to the tissue in the human body, and thus the ultrasound signal is generated based on the photoacoustic effect. The second way is to dispose at least one ultrasound transducer on the wire 110, and the ultrasound transducer emits the ultrasound signal. In either way, the signal detector 130 receives the ultrasound signal which is transmitted to the computer system 140 for calculating position information according to the ultrasound signal. The position information indicates the position of the wire 110 relative to the signal detector. The computer system 140 transmits the position information to the positioning module (i.e. the first driving unit 161 and the second driving unit 162). In some embodiments, the diameter of the wire 110 is less than 2 millimeters.

Figure 3:
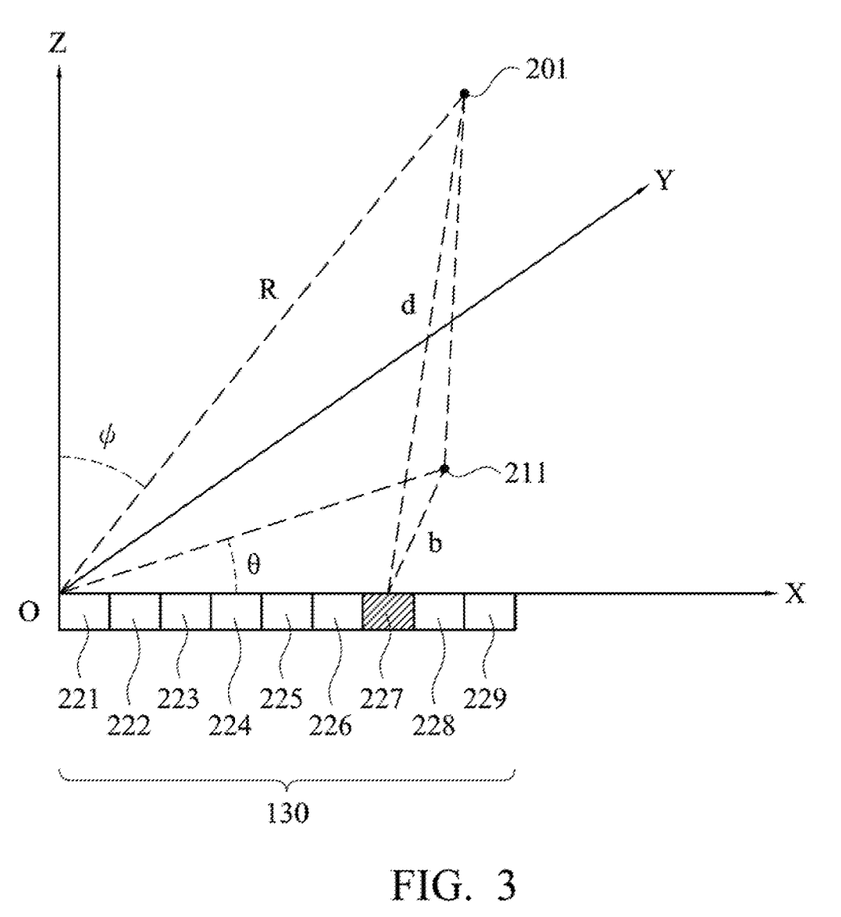
FIG. 3 is a diagram illustrating the calculation of the position of ultrasound transducers according to an embodiment.
Figure 4:
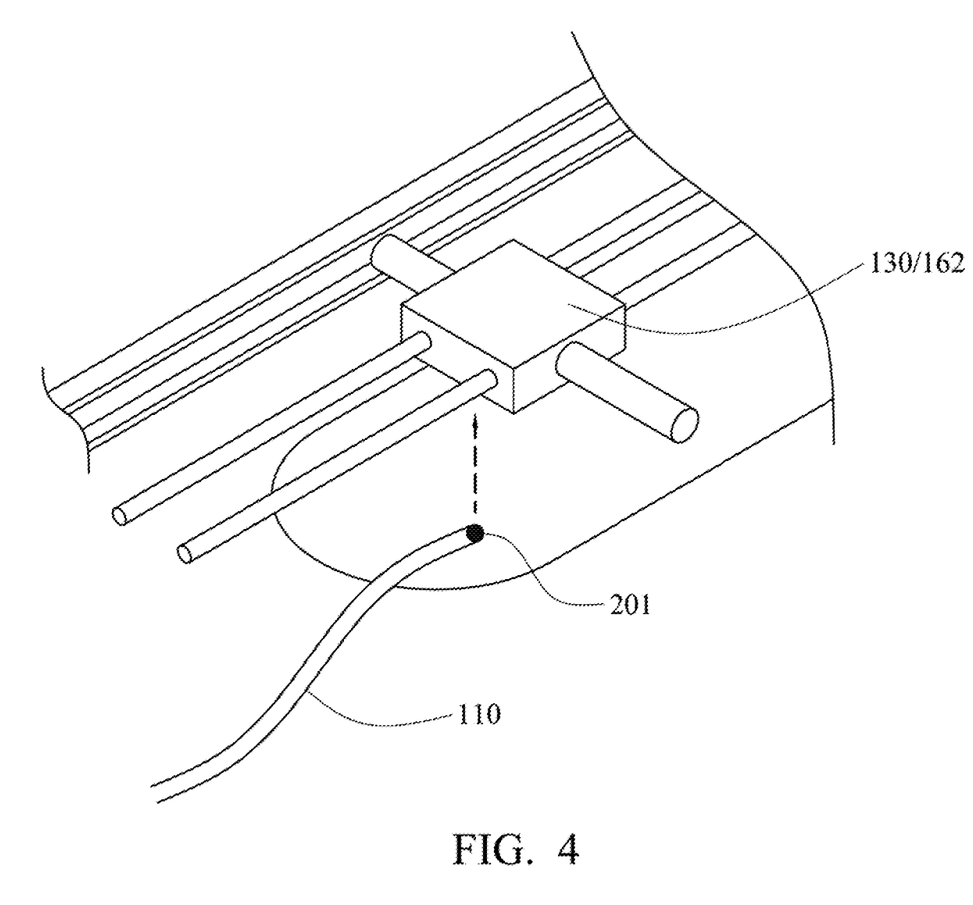
FIG. 4 is a diagram illustrating the signal detector 130 tracking the wire according to an embodiment.

Examples are provided herein to describe how to calculate the position of the wire when ultrasound transducers are disposed on the wire. FIG. 3 is a diagram illustrating the calculation of the position of ultrasound transducers according to an embodiment. FIG. 4 is a diagram illustrating the signal detector 130 tracking the wire according to an embodiment. Referring to FIG. 3 and FIG. 4, assume an ultrasound transducer 201 is disposed on the wire 110, and the signal detector 130 includes ultrasound transducers 221-229. Polar coordinates are used to describe the position of the ultrasound transducer 201. R is a distance between the ultrasound transducer 201 and an original point O. $\varphi$ is an angle of the ultrasound transducer 201 relative to a Z axis. A coordinate point 211 is a projection of the ultrasound transducer 201 on a X-Y plane. $\Theta$ is an angle of the coordinate point 211 relative to a X axis. The ultrasound transducer 221-229 are disposed on the X axis. Take the ultrasound transducer 227 as an example, the distance between the ultrasound transducer 201 and the ultrasound transducer 227 is d which is represented by a following equation (1).

$$d^2 = (R\cos\varphi)^2 + b^2 \qquad (1)$$
$$= R^2\cos^2\varphi + (R\sin\varphi\sin\theta)^2 + (R\sin\varphi\cos\theta - x_i)^2$$
$$= R^2\cos^2\varphi + R^2\sin^2\varphi\sin^2\theta + R^2\sin^2\varphi\cos^2\theta +$$
$$x_i^2 - 2R\sin\varphi\cos\theta$$
$$= R^2 + x_i^2 - 2R\sin\varphi\cos\theta$$

b is the distance between the coordinate point 211 and the ultrasound transducer 227. $x_i$ is the distance between the ultrasound transducer 227 and the original point O. Therefore, the time for the ultrasound signal propagating from the ultrasound transducer 201 to the ultrasound transducer 227 is $t_i$ which is represented by a following equation (2).

$$t_i = \frac{\sqrt{R^2 + x_i^2 - 2R\sin\varphi\cos\theta}}{c} \qquad (2)$$

c is the velocity of the ultrasound signal. In general, the velocity of the ultrasound signal in different tissues of human body are basically the same, and thus the velocity c could be constant. However, there may be air between the ultrasound transducer 201 and the ultrasound transducer 227, and the velocity of the ultrasound signal in the air is different from that in the tissues of human body. Therefore, after considering the effect of air, the equation (2) is modified as a following equation (3).

$$t_i = \frac{\sqrt{R^2 + x_i^2 - 2R\sin\varphi\cos\theta} - y}{c_1} + \frac{y}{c_2} \qquad (3)$$

y is the distance that the ultrasound signal propagates in air. The distance y is greater or equal to 0 and less than the distance d. $c_1$ is the velocity of the ultrasound signal propagating in a tissue of human body, and $c_2$ is the velocity of the ultrasound signal propagating in the air. The two velocities $c_1$, $c_2$ should be known. Note that the distance R, the angle $\varphi$, the angle $\theta$, and the distance y are unknown.

On the other hand, after the ultrasound transducers 221-229 receive the ultrasound signal, the practical time of the ultrasound signal transmitted to the ultrasound transducers 221-229 can be obtained and herein is respectively denoted as $\tau_1 \ldots \tau_N$, where N is a positive integer. The positive integer is 9 in the embodiment of FIG. 3. Next, a following optimization algorithm is performed to obtain the unknown variables.

$$\min_{R,\varphi,\theta,y} \sum_i \left(\frac{\sqrt{R^2 + x_i^2 - 2R\sin\varphi\cos\theta} - y}{c_1} + \frac{y}{c_2} - \tau_i\right)^2 \qquad (4)$$

$$s.b. \quad 0 \le y \le \sqrt{R^2 + x_i^2 - 2R\sin\varphi\cos\theta} \qquad (5)$$

The equation (4) is an objective function, and the equation (5) is the constraint. The positive integer i is from 1 to N (corresponding to the ultrasound transducer 221-229). In other words, the equation (4) is to calculate the optimal distance R, the angle φ, the angle θ, and the distance y so that the difference between the estimated time $t_i$ and the practical time $\tau_i$ is minimized. Because the equation (4) has four variables, the number (i.e. the positive number N) of the ultrasound transducers 221-229 has to be greater or equal to 4. After the distance R, the angle φ and the angle θ are obtained, the position of the ultrasound transducer 201 relative to the signal detector 130 is obtained, and therefore the first driving unit 161 and the second driving unit 162 are able to move the signal detector 130 to a position corresponding to a position of the wire 110 in the blood vessel of human body. As a result, healthcare provides just need to control the direction of the wire 110 with no need to manually control the signal detector 130.

In another embodiment, the wire 110 is an optical fiber. Laser ray is emitted into a first terminal of the optical fiber, and is emitted out from a second terminal of the optical fiber to a tissue in the human body. The wavelength of the laser ray may be in any suitable range. However, different human tissues have different absorption rates for different wavelength of light, and the effect of the photoacoustic imaging is better when the absorption rate is high. For example, blood has relatively higher absorption rate for 520 nm to 532 nm of wavelength, blood vessel has relatively higher absorption rate for about 1064 nm of wavelength, and fat has relatively higher absorption rate for about 1720 nm of wavelength. An objective of the invention is to track the wire in the blood vessel, and the tissue near the wire is blood or blood vessel. Therefore, the wavelength of the laser ray is ranged between 520 nm and 532 nm, or is about 1064 nm in some embodiments. The algorithm to calculate the position according to the ultrasound signal is similar to that described in FIG. 3, and there it will not be repeated. Alternatively, other suitable algorithms may be used to calculate the position corresponding to the wire according to the ultrasound signal in other embodiments, which is not limited in the invention.

In some embodiments, after the signal detector 130 receives the ultrasound signal, the computer system 140 can generate a first image accordingly. The position of the ultrasound transducer on the wire 110 in the position of blood is rendered on the first images. In addition, the signal detector 130 may emit another ultrasound signal toward the human body, the reflected ultrasound signal is received by the signal detector 130, and the computer system 140 may generate a second image accordingly. Tissues of human body are rendered in the second image (i.e. a conventional ultrasound image). The computer system 140 may combine the first image into the second image to generate a third image, in which the tissues of human body and the position of the ultrasound transducer on the wire 110 are rendered. Accordingly, healthcare providers can see where the wire 110 is in the human body via the third image.

Figure 5:
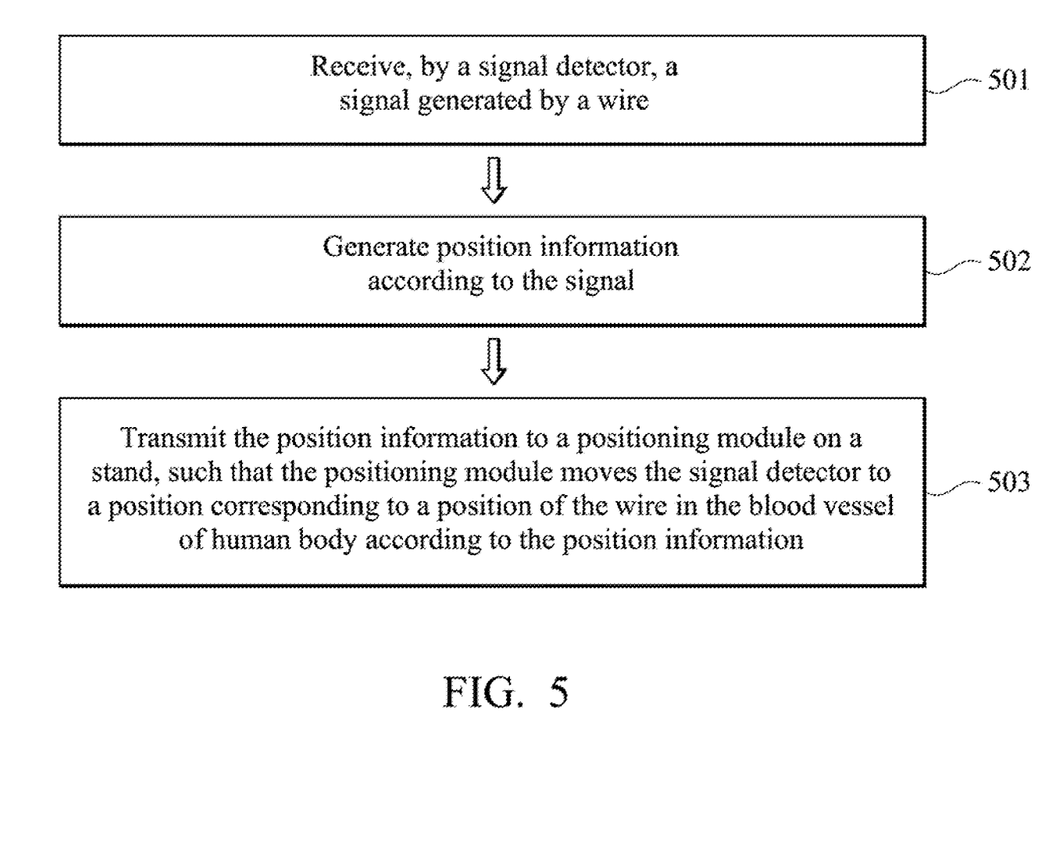
FIG. 5 is a diagram illustrating a flow chart of a method for tracking a wire according to an embodiment.

FIG. 5 is a diagram illustrating a flow chart of a method for tracking a wire according to an embodiment. Referring to FIG. 5, in step 501, a signal generated by a wire is received by a signal detector. In step 502, position information is generated according to the signal. In step 503, the position information is transmitted to a positioning module on a stand, such that the positioning module moves the signal detector to a position corresponding to a position of the wire in the blood vessel of human body according to the position information. However, each step has been described in detail above, and the description will not be repeated again. Note that each step of FIG. 5 may be implemented as programs or circuits, which is not limited in the invention. In addition, the method of FIG. 5 may be performed with the embodiments described above, and may also be performed independently. In other words, other steps may be inserted into the steps of FIG. 5.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system for tracking a wire in a blood vessel in a human body, wherein the system comprises:

a stand, surrounding a working area;

a signal detector, configured to receive a signal generated by the wire;

a positioning module disposed on the stand, and configured to drive the signal detector to move forward and backward on a two-dimensional plane in the working area; and a computer system, electrically connected to the signal detector and the positioning module, and configured to receive the signal from the signal detector, generate position information according to the signal, and transmit the position information to the positioning module, such that the positioning module moves the signal detector to a position corresponding to a position of the wire in the blood vessel according to the position information, wherein the signal is an ultrasound signal, the signal detector is an ultrasound detector, and at least one ultrasound transducer is disposed on the wire to emit the ultrasound signal, wherein generating the position information comprises:

the computer system performing the following equations (1) and (2) to calculate a position of the at least one ultrasound transducer on the wire relative to the ultrasound detector, $$\min_{R,\varphi,\theta,y} \sum_i \left( \frac{\sqrt{R^2 + x_i^2 - 2R\sin\varphi\cos\theta} - y}{c_1} + \frac{y}{c_2} - \tau_i \right)^2 \quad (1)$$

$$s.b. \quad 0 \leq y \leq \sqrt{R^2 + x_i^2 - 2R\sin\varphi\cos\theta}, \quad (2)$$

wherein R is a distance between the at least one ultrasound transducer and an original point, φ is an angle of the at least one ultrasound transducer relative to a Z axis, a coordinate point is projection of the at least one ultrasound transducer on a X-Y plane, θ is an angle of the coordinate point relative to a X axis, y is a distance that the ultrasound signal propagates in air, $x_i$ is a distance between an $i^{th}$ ultrasound transducer of a plurality of ultrasound transducers in the signal detector and the original point, $c_1$ is a velocity of the ultrasound signal propagating in an tissue, $c_2$ is a velocity of the ultrasound signal propagating in the air, and $\tau_i$ is time of the ultrasound signal propagating from the at least one ultrasound transducer to the $i^{th}$ ultrasound transducer, wherein a first track is formed on the stand, and the positioning module comprises:
  a first driving unit, disposed on the first track;
  a first support structure, disposed perpendicular to the first track and connected to the first driving unit; and
  a second driving unit, disposed on the first support structure, wherein the signal detector is connected to the second driving unit,
  wherein the first driving unit drives the first support structure along the first track, and the second driving unit moves along the first support structure.

2. The system of claim 1, wherein a second track is formed on the stand, the second track is perpendicular to the first track, the first track and the second track surround the working area, and the positioning module further comprises:
  a second support structure, disposed on the second track and connected to the second driving unit.

3. The system of claim 1, wherein the wire is an optical fiber for delivering light to a tissue in the human body such that the ultrasound signal is generated based on photoacoustic effect.

4. A method for a computer system to track a wire in a blood vessel of a human body, wherein the method comprises:
  receiving, by a signal detector, a signal generated by the wire;
  generating position information according to the signal; and
  transmitting the position information to a positioning module on a stand, wherein the stand surrounds a working area, the positioning module is configured to drive the signal detector to move forward and backward on a two-dimensional plane in the working area,
  wherein after the positioning module receives the position information, the positioning module moves the signal detector to a position corresponding to a position of the wire in the blood vessel according to the position information, wherein the signal is an ultrasound signal, the signal detector is an ultrasound detector, at least one ultrasound transducer is disposed on the wire to emit the signal, and the step of generating the position information comprises:
performing following equations (1) and (2) to calculate a position of the at least one ultrasound transducer on the wire relative to the signal detector, $$\min_{R,\varphi,\theta,y} \sum_i \left( \frac{\sqrt{R^2 + x_i^2 - 2R\sin\varphi\cos\theta} - y}{c_1} + \frac{y}{c_2} - \tau_i \right)^2 \quad (1)$$

$$s.b. \ 0 \le y \le \sqrt{R^2 + x_i^2 - 2R\sin\varphi\cos\theta}, \quad (2)$$

wherein R is a distance between the at least one ultrasound transducer and an original point, $\varphi$ is an angle of the at least one ultrasound transducer relative to a Z axis, a coordinate point is projection of he at least one ultrasound transducer on a X-Y plane, $\theta$ is an angle of the coordinate point relative to a X axis, y is a distance that the ultrasound signal propagates in air, $x_i$ is a distance between an $i^{th}$ ultrasound transducer of a plurality of ultrasound transducers in the signal detector and the original point, $c_1$ is a velocity of the ultrasound signal propagating in an tissue, $c_2$ is a velocity of the ultrasound signal propagating in the air, and $\tau_i$ is time of the ultrasound signal propagating from the at least one ultrasound transducer to the $i^{th}$ ultrasound transducer, wherein a first track is formed on the stand, and the positioning module comprises:
  a first driving unit, disposed on the first track;
  a first support structure, disposed perpendicular to the first track and connected to the first driving unit; and
  a second driving unit, disposed on the first support structure, wherein the signal detector is connected to the second driving unit,
  wherein the first driving unit drives the first support structure along the first track, and the second driving unit moves along the first support structure.

* * * * *